(12) United States Patent
Choi et al.

(10) Patent No.: US 9,193,761 B2
(45) Date of Patent: Nov. 24, 2015

(54) **METHOD FOR PURIFYING HUMAN GRANULOCYTE-COLONY STIMULATING FACTOR FROM RECOMBINANT *E. COLI***

(75) Inventors: Sung Chul Choi, Suwon-si (KR); Jin Ki Kim, Pyeongtaek-si (KR); Young Hak Oh, Suwon-si (KR); Jong Soo Lee, Seongnam-si (KR)

(73) Assignee: HANMI SCIENCE CO., LTD, Hwaseong-si (KR)

( * ) Notice: Subject to any disclaimer, the term of this patent is extended or adjusted under 35 U.S.C. 154(b) by 0 days.

(21) Appl. No.: 13/881,637

(22) PCT Filed: Oct. 26, 2011

(86) PCT No.: PCT/KR2011/008046
§ 371 (c)(1),
(2), (4) Date: Apr. 25, 2013

(87) PCT Pub. No.: WO2012/057529
PCT Pub. Date: May 3, 2012

(65) Prior Publication Data
US 2013/0211054 A1    Aug. 15, 2013

(30) Foreign Application Priority Data

Oct. 29, 2010 (KR) .................. 10-2010-0106994

(51) Int. Cl.
*C07K 1/36* (2006.01)
*C07K 14/535* (2006.01)

(52) U.S. Cl.
CPC ............. *C07K 1/36* (2013.01); *C07K 14/535* (2013.01)

(58) Field of Classification Search
None
See application file for complete search history.

(56) References Cited

U.S. PATENT DOCUMENTS

| 6,605,697 | B1 | 8/2003 | Kwon et al. |
| 2004/0224393 | A1 | 11/2004 | Kwon et al. |
| 2007/0004904 | A1 | 1/2007 | Nissen et al. |

FOREIGN PATENT DOCUMENTS

CA    1341389 C    10/2002

OTHER PUBLICATIONS

Vanz et al., "Human granulocyte colony stimulating factor (hG-CSF) : cloning, overexpression, purification and characterization", Microbial Cell Factories, Apr. 4, 2008, pp. 13 (1-12), vol. 7.
Zaveckas et al., "Mutation of surface-exposed histidine residues of recombinant human granulocyte-colony stimulating factor (Cys17Ser) impacts on interaction with chelated metal ions and refolding in aqueous two-phase systems", Journal of Chromatography B, 2003, pp. 17-32, vol. 786.
Lasnik et al., "Human granulocyte colony stimulating factor (hG-CSF) expressed by methylotrophic yeast Pichia pasforis", Pflugers Archiv-European Journal of Physiology, 2001, pp. R184-R186, vol. 442.
Bae et al., "Improved process for production of recombinant yeast-derived monomeric human G-CSF", Applied Microbiology and Biotechnology, 1999, pp. 338-344, vol. 52.
International Searching Authority, International Search Report of PCT/KR2011/008046 dated May 7, 2012.

*Primary Examiner* — Brian J Gangle
*Assistant Examiner* — Andrea McCollum
(74) *Attorney, Agent, or Firm* — Sughrue Mion, PLLC (57) ABSTRACT

The present invention provides a method for purifying a large amount of human granulocyte-colony stimulating factors (hG-CSFs) from a recombinant *E. coli* with high yield and purity. According to the method of the present invention, human granulocyte-colony stimulating factor, identical to the native form expressed in the human body, can be easily purified with high yield and purity without an additional activation process. In particular, according to the purification method of the present invention, hG-CSF variants expressed in *E. coli* are efficiently removed to obtain physiologically active hG-CSFs with high purity.

19 Claims, 3 Drawing Sheets

METHOD FOR PURIFYING HUMAN GRANULOCYTE-COLONY STIMULATING FACTOR FROM RECOMBINANT E. COLI

TECHNICAL FIELD

The present invention relates to a method for purifying human granulocyte-colony stimulating factors (hG-CSFs) from a recombinant E. coli. More particularly, the present invention relates to a method for purifying human granulocyte-colony stimulating factors (hG-CSFs) from a recombinant E. coli with high purity and yield, comprising the steps of (a) culturing an hG-CSF-expressing recombinant E. coli to obtain a cell pellet by centrifugation; (b) separating an hG-CSF-containing supernatant from the cell pellet obtained in step (a); (c) treating the supernatant obtained in step (b) with an acid to separate the resulting precipitate by filtration; (d) applying a filtrate obtained in step (c) to cation exchange chromatography; (e) applying an eluate obtained in step (d) to hydrophobic-interaction chromatography; and (f) applying an eluate obtained in step (e) to anion exchange chromatography.

BACKGROUND ART

Colony stimulating factors (CSF) are produced by T-cells, macrophages, fibroblasts, and endothelial cells, and these cells are widely distributed throughout the body. The known CSFs include GM-CSF, M-CSF, and G-CSF. Among them, GM-CSF is a granulocyte macrophage-colony stimulating factor, and acts on stem cells of granulocytes or macrophages to induce their proliferation and differentiation, thereby stimulating colony formation of granulocytes or macrophages. M-CSF (macrophage-CSF) is a macrophage-colony stimulating factor, and primarily functions to stimulate colony formation of macrophages. G-CSF (granulocyte-CSF) is a granulocyte-colony stimulating factor, and stimulates colony formation of granulocytes and induces the final differentiation.

Conventionally, in order to isolate and purify G-CSF, cells are cultured and G-CSF proteins are isolated from the culture supernatant. However, this method has a problem of the low yield of G-CSF, and thus is not suitable for mass-production. In addition, Chugai Pharmaceuticals Co., Ltd. (Japan) has developed a method of producing glycosylated hG-CSF in a mammalian cell by employing a genomic DNA or cDNA including a polynucleotide encoding hG-CSF (Korean Patent NOS. 47178, 53723 and 57582). However, it is known that the sugar chain of glycosylated hG-CSF is not necessary for the activity of hG-CSF and the production of glycosylated hG-CSF employing mammalian cells requires expensive materials and facilities, and therefore, such a process is not economically feasible.

There have been attempts to produce non-glycosylated hG-CSF by employing a prokaryotic cell. In these studies, hG-CSFs having a methionine residue attached at the N-terminus thereof due to the ATG initiation codon are produced, but this form is different from the native form. Further, hG-CSF produced in a microorganism may be contaminated with impurities derived from host cells or culture materials, and a complicated purification process is required for application to high-purity medicine. Furthermore, when E. coli is used as a host cell, most of the hG-CSFs are deposited in the cells as insoluble inclusion bodies, and they must be converted to an active form through a refolding process, at a significant loss of yield. During the process, partial reduction, intramolecular disulfide formation or erroneous disulfide formation is induced, and thus a cumbersome process is needed to remove them and loss of potency is caused. One cysteine residue does not participate in forming the disulfide bond, and thus exist in a free form, resulting in additional loss of potency and reduction of stability in a protein solution.

Accordingly, there is a need to develop a method for mass-producing hG-CSFs that have no methionine residue at their N-terminus and thus are identical to the native form even though using microorganisms.

In order to solve the problems, the present inventors have previously reported that a new secretory signal peptide with high expression rate is prepared by modifying the known signal peptide of E. coli thermoresistant enterotoxin II (Korean Patent No. 316347) and used to produce native hG-CSF. Further, the present inventors have prepared an expression vector including a recombinant gene that is prepared by linking the hG-CSF gene, instead of enterotoxin gene, next to the modified signal peptide of E. coli thermoresistant enterotoxin II, and they have transformed E. coli with the expression vector, thereby expressing biologically active hG-CSFs in the periplasm by employing a microbial secretory system (Korean Patent No. 356140).

By using the microbial system of secreting a protein into the periplasm, native hG-CSFs having no methionine residue at the N-terminus can be obtained in a soluble form. Further, the periplasmic proteins are normally less than 10% of the total cell protein and thus, so less extensive purification of the recombinant protein is required than for proteins located in the cytoplasm. Furthermore, a procedure of cell disruption is not needed, and contamination with saccharides and nucleic acids present in the cytoplasm can be minimized. However, because of low expression level in the periplasmic production, its industrialization is difficult. Therefore, there is an urgent need to develop an efficient method for purifying expressed proteins with high yield and purity.

DISCLOSURE

Technical Problem

Accordingly, the present inventors have endeavored to address the problems of the prior art. As a result, they found that native human granulocyte-colony stimulating factors can be mass-produced with high purity by culturing recombinant E. coli to obtain secretory proteins, and then applying the proteins to acid precipitation→cation exchange chromatography→hydrophobic-interaction chromatography→anion exchange chromatography in this order, thereby completing the present invention.

Technical Solution

An object of the present invention is to provide a method for purifying human granulocyte-colony stimulating factors (hG-CSFs) from a recombinant E. coli with high purity and yield, comprising the steps of:

(a) culturing an hG-CSF-expressing recombinant E. coli to obtain a cell pellet by centrifugation;

(b) separating an hG-CSF-containing supernatant from the cell pellet obtained in step (a);

(c) treating the supernatant obtained in step (b) with an acid to separate the resulting precipitate by filtration;

(d) applying a filtrate obtained in step (c) to cation exchange chromatography;

(e) applying an eluate obtained in step (d) to hydrophobic-interaction chromatography; and (f) applying an eluate obtained in step (e) to anion exchange chromatography.

Another object of the present invention is to provide physiologically active, variant-free hG-CSFs with high purity that are isolated and purified from the recombinant *E. coli* by the above method.

Advantageous Effects

According to the method of the present invention, human granulocyte-colony stimulating factor, identical to the native form expressed in the human body, can be easily purified with high yield and purity without an additional activation process. In particular, according to the method of the present invention, hG-CSF variants expressed in *E. coli* are efficiently removed to obtain physiologically active hG-CSFs with high purity.

DESCRIPTION OF DRAWINGS

FIG. 1 shows the results of SDS-PAGE of each solution obtained from the steps of osmotic extraction, acid precipitation, cation exchange chromatography, and hydrophobic-interaction chromatography of hG-CSFs that are purified from the periplasm of recombinant *E. coli* according to the purification method of the present invention, in which
   Lane 1: Standard
   Lane 2: Supernatant of primary centrifugation of step (b)
   Lane 3: Supernatant of secondary centrifugation of step (b)
   Lane 4: Supernatant obtained by acid precipitation of step (c)
   Lane 5: Filtrate obtained by filtration of step (c)
   Lane 6: Column flow of SP-SEPHAROSE column of step (d)
   Lane 7: Column eluate 1 flow of SP-SEPHAROSE column of step (d)
   Lane 8: Column eluate 2 flow of SP-SEPHAROSE column of step (d)
   Lane 9: Column flow 2 flow of butyl-SEPHAROSE column of step (e)
   Lane 10: Column eluate 2 flow of butyl-SEPHAROSE column of step (e);

BEST MODE

The present invention provides a method for simply purifying a large amount of human granulocyte-colony stimulating factors (hG-CSFs) with high purity from a recombinant *E. coli* without an additional activation process.

Specifically, the purification method according to the present invention may include the steps of:
   (a) culturing an hG-CSF-expressing recombinant *E. coli* to obtain a cell pellet by centrifugation;
   (b) separating an hG-CSF-containing supernatant from the cell pellet obtained in step (a);
   (c) treating the supernatant obtained in step (b) with an acid to separate the resulting precipitate by filtration;
   (d) applying a filtrate obtained in step (c) to cation exchange chromatography;
   (e) applying an eluate obtained in step (d) to hydrophobic-interaction chromatography; and
   (f) applying an eluate obtained in step (e) to anion exchange chromatography.

The purification method according to the present invention is characterized in that after acid precipitation, hG-CSFs obtained from recombinant *E. coli* are applied to a series of chromatography steps (cation exchange chromatography, hydrophobic-interaction chromatography and anion exchange chromatography), thereby isolating highly pure hG-CSFs suitable for pharmaceutical use.

Hereinafter, each step of the purification method according to the present invention will be described in detail.

Step (a) is a step of culturing an hG-CSF-expressing recombinant *E. coli* to obtain a cell pellet by centrifugation. The recombinant *E. coli* used in this step is any one expressing hG-CSF, preferably any one expressing hG-CSF in the periplasm, without limitation. More preferably, the hG-CSFs of the present invention are soluble hG-CSFs expressed in *E. coli*. In the present invention, the recombinant *E. coli* expressing hG-CSFs in the periplasm is a recombinant *E. coli* that is transformed with an expression vector including a fusion gene encoding a fusion protein of secretory signal sequence and hG-CSF. Representative examples of the recombinant *E. coli* include HM10310, HM10311 (KCCM-10154), HM10409, HM10410 (KCCM-10151), HM10411 (KCCM-10152), HM10413, HM10414, HM10415, HM10510 (KCCM-10153), HM10511, and HM10512 disclosed in Korean Patent No. 356140 of the present inventors and its counterpart U.S. Pat. No. 7,704,709, in which the recombinant *E. coli* is transformed with an expression vector prepared by fusion of a modified signal peptide of *E. coli* thermoresistant enterotoxin II and hG-CSF, but are not limited thereto. Recombinant *E. coli* HM10311, HM10410, HM10411 and HM10510 are deposited under the Budapest Treaty on the International Recognition of theDeposit of Microorgansims For the Purposes of Patent Procedure on Mar. 24, 1999 at Korean Culture Center of Microorgansims (KCCM) at Department of Food Engineering College of Eng., Yonsei University of Sodaemun-gu, Seoul 120-749, Republic of Korea, under Accession Numbers KCCM-10154, KCCM-10151, KCCM-10152, KCCM-10153, respectively.

In order to express hG-CSF in the periplasm of the recombinant *E. coli*, the recombinant *E. coli* may be cultured by fed-batch culture in a fermentor containing an LB medium supplemented with 1 to 300 g/L of glucose as a carbon source, 2 to 15 g/L of $KH_2PO_4$, 0.5 to 3 g/L of $(NH_4)_2HPO_4$, 2 to 10 g/L of NaCl and 0.5 to 10 g/L of $MgCl_2$ as minerals, a variety of trace elements, yeast extract, and tryptone. This medium composition is suitable for high density culture of recombinant *E. coli* and high expression of hG-CSF in the periplasm of *E. coli*. In one preferred embodiment of the present invention, the recombinant *E. coli* HM10411 (KCCM-10152) was used to perform an experiment, and as a result, the medium composition was found to greatly increase the cell density of the recombinant *E. coli*, the expression level of hG-CSF in *E. coli*, and secretion rate of hG-CSF into the periplasm. The obtained culture broth of recombinant *E. coli* is centrifuged to obtain a cell pellet.

Step (b) is a step of separating an hG-CSF-containing supernatant from the cell pellet obtained in step (a). In a preferred embodiment of the present invention, when the recombinant *E. coli* expressing hG-CSFs into the periplasm is used, periplasmic proteins including hG-CSFs can be separated from the cells by osmotic extraction. In this regard, step (b) may include the steps of adding a sucrose-containing buffer solution to the cell pellet to obtain a cell pellet by centrifugation; and adding distilled water to the cell pellet to obtain a supernatant containing periplasmic proteins by centrifugation. In this step, the periplasmic proteins including hG-CSFs are extracted by osmotic pressure. First, when the cell pellet is treated with the sucrose-containing buffer solution, for example, a 10% to 30% sucrose-containing buffer solution, the cells shrink. Then, when the cell pellet is treated with distilled water again, the shrunken cells expand and the cell wall is loosened. Therefore, the cell wall is not disrupted, but the periplasmic proteins including hG-CSFs present between the cell membrane and the cell wall are extracted through the loosened cell wall. In the osmotic extraction of step (b), sucrose, glucose, MgC12, sodium chloride or the like may be used. Preferably, the sucrose buffer solution is used. The extract was centrifuged to obtain a periplasmic protein-containing supernatant.

Step (c) is an acid precipitation step of treating the hG-CSF-containing supernatant obtained in step (b) with an acid to separate the resulting precipitate by filtration. In one preferred embodiment of the present invention, when the recombinant *E. coli* expressing hG-CSFs into the periplasm is used, a soluble hG-CSF-containing supernatant can be separated from the supernatant including periplasmic proteins by acid precipitation. Specifically, when the supernatant obtained in step (b) is treated with an acid to adjust pH of the supernatant to 5.0 to 5.8, preferably 5.3 to 5.5, insoluble materials including periplasmic proteins in the supernatant are precipitated, and this precipitate is removed by filtration so as to obtain a soluble hG-CSF-containing supernatant. Examples of the acid suitable for the acid precipitation of step (c) include acetic acid, phosphoric acid, citric acid or the like, and preferably acetic acid. The filtration may be performed using a proper filter, and preferably 0.45 to 3 μm filter. Since the recombinant *E. coli* secreting hG-CSFs into the periplasm is used in the present invention, there is no need of disrupting *E. coli*, and the periplasm fraction can be easily obtained from the culture broth so as to extract hG-CSFs.

Step (d) is a step of applying a soluble hG-CSF-containing filtrate obtained in step (c) to cation exchange chromatography. Through this step, a large amount of impurities derived from host cells or culture materials can be removed to improve purification efficiency.

A column functional group of the cation exchange chromatography used in the present invention may include weak cations such as carboxymethyl- (CM-) and carboxy- (C-) and strong cations such as sulfo- (S-), sulfomethyl- (SM-), sulfoethyl- (SE-), sulfopropyl- (SP-), and phospho- (P-). A variety of column resins may be used, including SEPHAROSE (cross-linked agarose), SEPHADEX (cross-linked dextran gel), agarose, SEPHACEL (cross-linked cellulose resin), polystyrene, polyacrylate, cellulose, and TOYOPEARL (silica resin). In one preferred embodiment of the present invention, the purification method may be performed by cation exchange chromatography using a SP-SEPHAROSE column.

In the present invention, the cation exchange chromatography is performed using an acetic acid-containing buffer solution as an eluent within the pH ranging from pH 4.0 to 6.0, preferably pH 5.0 to 6.0 at a salt concentration of 500 mM or less, preferably 200 to 500 mM. The cation exchange column to be used may be equilibrated with a buffer solution before loading the eluate. The equilibration of cation exchange column may be performed using an aqueous buffer solution of pH 5.0 to 6.0, which is properly selected according to the conditions. In one preferred embodiment of the present invention, the cation exchange column is equilibrated with a 10 mM sodium acetate-containing buffer solution (pH 5.4) in advance. After the hG-CSF-containing filtrate is loaded and adsorbed onto the equilibrated cation exchange column, the column is washed with the equilibration buffer solution so as to remove the proteins and impurities that are not adsorbed onto the column. Subsequently, an elution buffer solution prepared by addition of sodium chloride to the equilibration buffer solution is applied to the cation exchange column, so as to elute hG-CSFs that are adsorbed onto the column. In this regard, 3 to 7 column volumes of the elution buffer solution are preferably applied. In one preferred embodiment of the present invention, 4 to 6 column volumes of a buffer solution (pH 5.2 to 5.6) containing 5 to 20 mM sodium acetate and 300 to 400 mM NaCl are applied to the column so as to elute hG-CSFs that are adsorbed onto the column.

In the above step, the host cell-derived peptides or the components in the culture medium are passed through the column or removed out during a washing step, so as to effectively remove a large amount of impurities.

Step (e) is a step of (e) applying an eluate obtained from the cation exchange chromatography in step (d) to hydrophobic-interaction chromatography, and a step of improving purity by further removing impurities that are included in the eluate obtained from the cation exchange chromatography of the prior step.

The hydrophobic-interaction chromatography used in the present invention may be performed on gels with hydrophobic, suitably aliphatic or aromatic, charge-free ligands attached to various commercially available matrices. The ligands may be coupled to the matrix by conventional coupling techniques giving charge-free ligands. Examples of such technique include a method of using glycidyl-ether coupling; a method of activating an agarose matrix with glycidoxypropyltrimethoxy silane in water and then immobilizing the ligand in alcohol; a method of activating an agarose matrix with bis-epoxide, such as 1,4-butanediol diglycidyl ether and then coupling to ligands such as aminoalkyl or alkyl mercaptan; a 1,1-carbonyldiimidazole activation method; and a divinylsulfone activation method. The gels resulting from the above described techniques are charge-free within the entire pH-range. Examples of the aliphatic ligand may include straight alkyls such as propyl, butyl, pentyl, hexyl, heptyl and octyl, branched alkyls such as iso- or neoalkyl, and oligoethylene glycol. The aromatic ligand is preferably phenyl. The matrix may be properly selected from various strongly hydrophilic matrices, for example, an agarose matrix such as SEPHAROSE, an organic polymer matrix such as TSK-GEL (silica based gel), and a highly porous organic polymer matrix. The preferred matrix is an agarose matrix. A suitable agarose matrix is SEPHAROSE (Amersham Biosciences), BIO-GEL-A (Bio-Rad Laboratories), MINI-LEAK (Kem-En-Tec Diagnostics A/S) or the like. In one preferred embodiment of the present invention, the hydrophobic-interaction chromatography of the present invention is carried out in a butyl-SEPHAROSE gel.

In the present invention, the hydrophobic-interaction chromatography is performed using a buffer solution within the pH ranging from pH 7.0 to 8.5, preferably pH 7.5 to 8.0, having a salt concentration of 100 mM or less, preferably 0 to 50 mM as an eluent. The hydrophobic-interaction column to be used may be equilibrated with a buffer solution before loading the eluate. The equilibration of hydrophobic-interaction column may be performed using an aqueous buffer solution of pH 6.8 to 8.5, which is properly selected according to the conditions. In one preferred embodiment of the present invention, the hydrophobic-interaction column is equilibrated with a buffer solution (pH 7.5) containing 300 mM ammonium sulfate and 10 mM Tris in advance. After the eluate obtained in the prior step is loaded on the equilibrated hydrophobic-interaction column so as to adsorb hG-CSFs thereto, the column is washed with the equilibration buffer solution so as to remove the proteins and impurities that are not adsorbed onto the column. Subsequently, an elution buffer solution prepared by removing ammonium sulfate from the equilibration buffer solution is applied to the hydrophobic-interaction column, so as to elute hG-CSFs that are adsorbed onto the column. In this regard, 1 to 4 column volumes of the elution buffer solution are preferably applied. In one preferred embodiment of the present invention, 1.2 to 2.5 column volumes of a buffer solution (pH 7.0 to 8.0) containing 5 to 20 mM Tris are applied to the column so as to elute hG-CSFs that are adsorbed onto the column.

In general, before performing the hydrophobic-interaction chromatography, a salt may be added to a fraction in order to increase conductivity of the fraction. Thereafter, elution is performed from the matrix using a low ionic strength buffer. Preferably, in the hydrophobic-interaction chromatography of the present invention, ammonium sulfate is added to the eluate obtained in step (d), so as to increase its conductivity, similar to that of the equilibration buffer solution. Then, the eluate is loaded to the equilibrated hydrophobic-interaction column. In the hydrophobic-interaction chromatography of the present invention, the eluate obtained from the cation exchange chromatography of the prior step may be also loaded without pretreatment, and hG-CSFs are adsorbed onto the column. The impurities are passed through the column or removed out during a washing step, so as to further improve purification efficiency.

Step (f) is a step of applying an eluate obtained from the hydrophobic-interaction chromatography in step (e) to anion exchange chromatography, and a step of completely removing the impurities that are included in the eluate obtained from the hydrophobic-interaction chromatography of the prior step.

The anion exchange chromatography of the present invention is typically carried out using a matrix containing an insoluble particle support derivatized with a tertiary or quaternary amine group (e.g., diethylamnoethyl, triethylaminoethyl, benzyl-diethylaminoethyl). Suitable support includes cellulose, agarose, dextran and polystyrene beads. Preferably, the support is derivatized with the triethylaminoethyl group. Examples of the suitable anion exchange matrix include Q-SEPHAROSE (Amersham Biosciences), MACRO-PREP (polymethacrylate beads) Q (Bio-Rad Laboratories), Q-HYPER-D (hydrogel) (BioSepra, Inc.), FRACTOGEL(cross-linked polymethacrylate resins) EMD-TMAE 650 (Merck) or the like. In one preferred embodiment of the present invention, the anion exchange chromatography of the present invention is carried out using a Q-SEPHAROSE column.

In the present invention, the anion exchange chromatography is performed using a buffer solution within the pH ranging from pH 6.8 to 8.5, preferably pH 7.0 to 8.0 having a salt concentration of 300 mM or less, preferably 100 to 250 mM as an eluent. The anion exchange column to be used may be equilibrated with a buffer solution before loading the eluate. The equilibration of anion exchange column may be performed using an aqueous buffer solution of pH 6.8 to 8.5, which is properly selected according to the conditions. In one preferred embodiment of the present invention, the anion exchange column is equilibrated with a buffer solution (pH 7.5) containing 10 mM Tris and 100 mM urea in advance. After the eluate obtained in the prior step is loaded on the equilibrated anion exchange column so as to adsorb hG-CSFs thereto, the column is washed with the equilibration buffer solution so as to remove the proteins and impurities that are not adsorbed onto the column. Subsequently, an elution buffer solution prepared by addition of sodium chloride to the equilibration buffer solution is applied to the anion exchange column, so as to elute hG-CSFs that are adsorbed onto the column. In this regard, 1.5 to 5 column volumes of the elution buffer solution are preferably applied. In one preferred embodiment of the present invention, 2 to 4 column volumes of a buffer solution (pH 7.0 to 8.0) containing 5 to 20 mM Tris, 50 to 200 mM urea, and 150 to 250 mM NaCl are applied to the column so as to elute hG-CSFs that are adsorbed onto the column.

As described above, hG-CSFs are purified by the acid precipitation and a series of chromatography according to the present invention, and the purified hG-CSFs are subjected to reversed-phase high-performance chromatography and size exclusion chromatography. As a result, hG-CSF with purity of 99% or higher was obtained in a high yield. Specifically, the result of N-terminal sequence analysis showed that hG-CSF purified according to the method of the present invention has a sequence identical to that of native hG-CSF, and the purified hG-CSF contains the host cell-derived proteins of 100 ng/mg or less, the host cell-derived DNAs of 100 pg/mg or less, and enterotoxin of 10 EU/IU hG-CSF or less, and shows excellent physiological activity. These results suggest that, when hG-CSFs secreted into the periplasm of recombinant E. coli are purified according to the purification method of the present invention, hG-CSFs with high physiological activity and purity can be obtained in a high yield, and loss of potency and the limited selection of columns can be also overcome.

Therefore, the hG-CSFs purified according to the purification method of the present invention and a pharmaceutical composition comprising the hG-CSFs as an active ingredient are also included in the scope of the present invention.

Preparation of the pharmaceutical composition and effects thereof are well known to those skilled in the art, and thus a detail description thereof will be omitted.

Further, the purification method according to the present invention is characterized in that hG-CSFs can be purified with high yield and purity from a large amount of culture broth of the recombinant E. coli. As used herein, the term "a large amount of culture broth" means a culture broth obtained by culturing the recombinant E. coli at a fermentation level in a medium of 50 L or more, preferably 80 L or more, and more preferably 100 L or more. In one preferred embodiment of the present invention, the recombinant E. coli is inoculated in 1 L of sterilized medium to obtain a primary seed culture broth, and this seed culture broth is inoculated in 14 L of sterilized medium to obtain a secondary seed culture broth. Finally, the secondary seed culture broth is inoculated in 120 L of sterilized medium, followed by fermentation. Additional media is used to perform fed batch culture, thereby obtaining 180 L of culture broth of the recombinant E. coli. When hG-CSFs are isolated and purified from a large amount of culture broth of the recombinant E. coli according to the method described in Korean Patent No. 356140, only 70 mg of hG-CSFs per 1 L are produced. That is, the conventional method has a limitation in that it is difficult to produce the desired protein with high purity and yield. However, according to the purification method of the present invention, even though the volume of culture broth is scale-up to 100 L or more, hG-CSFs with purity of 99% or higher can be obtained in a high yield of 110 mg or more per 1 L via the acid precipitation and a series of chromatography. Therefore, the purification method according to the present invention can be effectively applied for isolation and purification of hG-CSFs from a large amount of culture broth of the recombinant *E. coli*. Thus, higher productivity can be achieved by industrial application thereof.

[Mode for Invention]

Hereinafter, the present invention will be described in more detail with reference to the following Examples. However, these Examples are for illustrative purposes only, and the invention is not intended to be limited by these Examples.

REFERENCE EXAMPLE 1

Cultivation of Recombinant *E. coli* Expressing hG-CSFs into Periplasm

*E. coli* HM10411 (KCCM-10152, Korean Patent No. 356140) transformed with an expression vector TO17SG having a fusion of a modified signal peptide of *E. coli* thermoresistant enterotoxin II and hG-CSF was inoculated in a glass culture vessel containing 1 L of an LB medium (tryptone 10 g/L, yeast extract 5 g/L, NaCl 10 g/L)) to perform a primary seed culture. The culture medium was cultured at 37° C. for 11 to 13 hours under vigorous stirring and ventilation, and then inoculated in a culture vessel containing 14 L of sterilized LB medium to perform a secondary seed culture for 2 to 3 hours. The obtained culture broth was used as a seed for fermentation, and inoculated in 120 L of sterilized medium supplemented with 1.4 g/L of glucose as a carbon source, 10 g/L of $KH_2PO_4$, 2.5 g/L of $(NH_4)_2HPO_4$, 5 g/L of NaCl and 1.2 g/L of $MgCl_2$ as minerals, a variety of trace elements, yeast extract, and tryptone. During the fermentation, additional glucose and yeast extract were added to perform a fed-batch culture for 25 hours or longer, and the culture was completed to give 180 L of culture broth. After completion of the fermentation, the fermented broth was centrifuged at 7,000 rpm, and the obtained cell pellet was stored at −70° C.

EXAMPLE 1

Purification of hG-CSFs from Culture Broth of Recombinant *E. coli*

<1-1> Osmotic Extraction of Periplasmic Proteins

The *E. coli* pellet obtained in Reference Example was suspended in 170 L of sucrose buffer solution (20% sucrose, 1 mM EDTA, 30 mM Tris, pH 7.5), and stirred for 90 minutes, followed by primary centrifugation at 7,000 rpm, and thus a pellet was separated. 170 L of distilled water at 4° C. was added to the separated pellet, and a secondary centrifugation was performed at 7,000 rpm to remove a pellet and to isolate a supernatant containing periplasmic proteins. During this procedure, proteins present in the periplasm of *E. coli* were extracted. The supernatants obtained in the primary and secondary centrifugation procedures were analyzed by SDS-PAGE (Lanes 2 and 3 of FIG. 1).

<1-2> Acid Precipitation

1% acetic acid was added to the periplasmic protein-containing supernatant obtained in Example <1-1> to adjust the pH to 5.6 to 5.7. At this time, insoluble materials included in the supernatant were precipitated by acid treatment, and filtration was performed to remove them, so as to obtain an hG-CSF-containing supernatant. The supernatant obtained by acid treatment and the filtrate obtained by filtration were analyzed by SDS-PAGE (Lanes 4 and 5 of FIG. 1).

<1-3> Cation Exchange Chromatography

Cation exchange chromatography of the filtrate obtained in Example <1-2> was performed using a SP-SEPHAROSE column as follows. The filtrate was loaded and adsorbed onto the SP-SEPHAROSE column equilibrated with a buffer solution 1 (10 mM sodium acetate, pH 5.4) at a flow rate of 40 cm/hr, and then proteins that are not adsorbed onto the column were removed by washing with the equal buffer solution. Subsequently, 5 column volumes of the buffer solution 1 (10 mM sodium acetate, pH 5.4) containing 300 mM sodium chloride are applied to the column so as to elute hG-CSFs from the column. The flow and the eluate obtained by the cation exchange chromatography were analyzed by SDS-PAGE (Lanes 6 to 8 of FIG. 1).

<1-4> Hydrophobic-interaction Chromatography

The eluate obtained in Example <1-3> was diluted by addition of ammonium sulfate to a final concentration of 300 mM, and hydrophobic-interaction chromatography was performed using a butyl-SEPHAROSE column as follows. The eluate was loaded and adsorbed onto the butyl-SEPHAROSE column equilibrated with a buffer solution 2 (300 mM ammonium sulfate, 10 mM Tris, pH 7.5) at a flow rate of 80 cm/hr, and then proteins that are not adsorbed onto the column were removed by washing with the equal buffer solution. Subsequently, 1.5 column volumes of the buffer solution 2 (10 mM Tris, pH 7.5) excluding ammonium sulfate are applied to the column so as to elute hG-CSFs from the column. The flow and the eluate obtained by the hydrophobic-interaction chromatography were analyzed by SDS-PAGE (Lanes 9 to 10 of FIG. 1).

<1-5> Anion Exchange Chromatography

The eluate obtained in Example <1-4> was diluted by addition of urea to a final concentration of 50 mM, and anion exchange chromatography was performed using a Q-SEPHAROSE column as follows. The eluate was loaded and adsorbed onto the Q-SEPHAROSE column equilibrated with a buffer solution 3 (10 mM Tris, pH 7.5, 100 mM urea) at a flow rate of 60 cm/hr, and then proteins that are not adsorbed onto the column were removed by washing with the equal buffer solution. Subsequently, 3 column volumes of the buffer solution 3 (10 mM Tris, pH 7.5, 100 mM urea) containing 250 mM sodium chloride are applied to the column so as to elute hG-CSFs from the column. The eluate obtained by the anion exchange chromatography was analyzed by SDS-PAGE (Lane 2 of FIG. 2).

In order to examine the purity of hG-CSFs purified from the recombinant *E. coli* by the procedures of Examples <1-1> to <1-5>, SDS-PAGE, N-terminal sequence analysis, reversed-phase high-pressure chromatography, and size exclusion high pressure chromatography were performed.

EXPERIMENTAL EXAMPLE 1

SDS-Page Analysis

Figure 1:
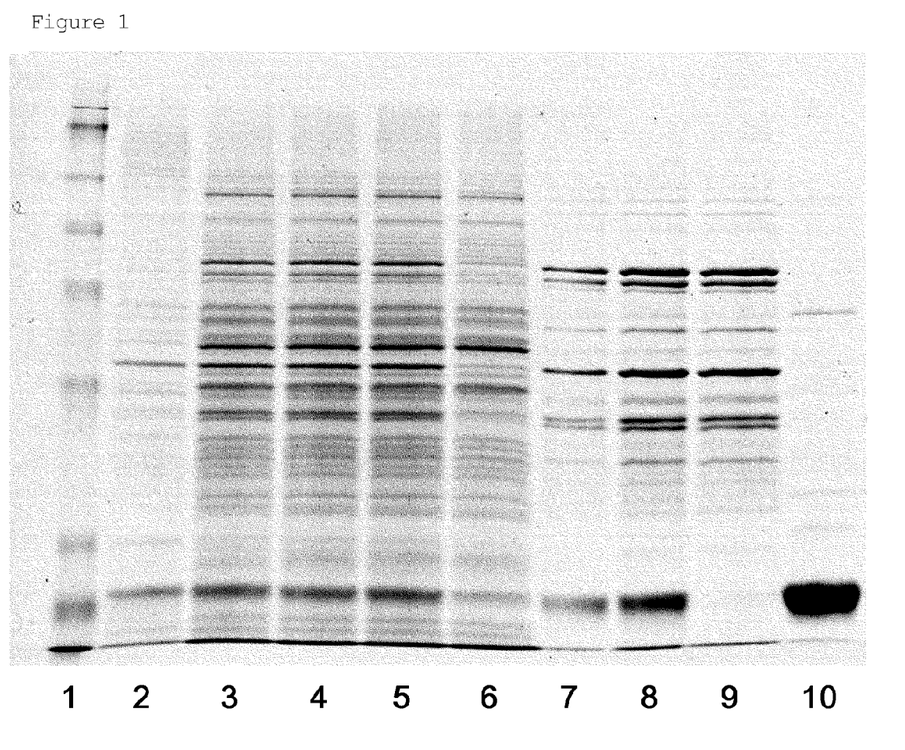
Figure 2:
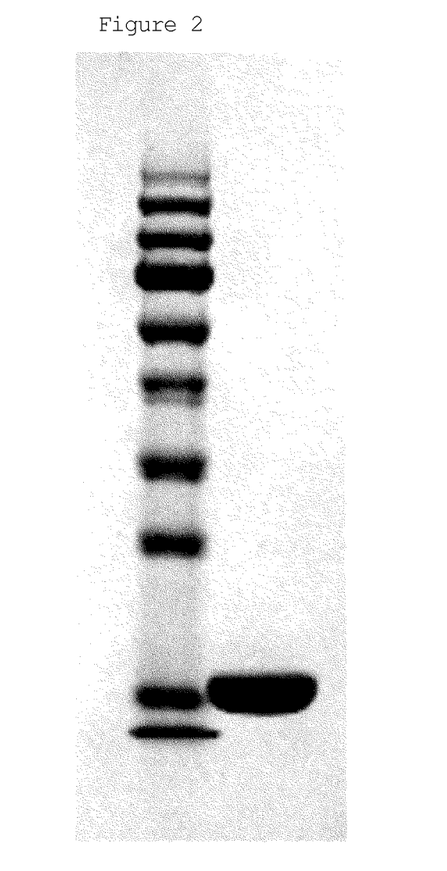
FIG. 2 shows the result of SDS-PAGE of the column eluate that is obtained by anion exchange chromatography of the purification method of the present invention.

First, the supernatant, the column flow, and the column eluate obtained in each procedure of Examples <1-1> to <1-5>, and a standard G-CSF (NIBSC, Code No. 88/502) were analyzed by SDS-PAGE according to a typical method. The results of SDS-PAGE are shown in FIGS. 1 and 2. In FIG. 1, Lane 1 is a standard G-CSF, Lane 2 is the supernatant of primary centrifugation obtained by osmotic extraction of Example <1-1>, Lane 3 is the supernatant of secondary centrifugation obtained by osmotic extraction of Example <1-1>, Lane 4 is the supernatant obtained by acid treatment in acid precipitation step of Example <1-2>, Lane 5 is the filtrate obtained by filtration in acid precipitation step of Example <1-2>, Lane 6 is the column flow obtained from SP-SEPHAROSE column chromatography of Example <1-3>, Lanes 7 and 8 are the column eluate 1 and 2 obtained from SP-SEPHAROSE column chromatography of Example <1-3>, Lane 9 is the column flow obtained from butyl-SEPHAROSE column chromatography of Example <1-4>, and Lane 10 is the column eluate obtained from butyl-SEPHAROSE column chromatography of Example <1-4>. In FIG. 2, Lane 1 is a standard Met-hG-CSF, and Lane 2 is the column eluate obtained from Q-SEPHAROSE column chromatography of Example <1-5>.

The results of SDS-PAGE analysis showed that hG-CSFs isolated and purified from the recombinant *E. coli* according to the purification method of the present invention have a molecular weight equal to that of native form.

EXPERIMENTAL EXAMPLE 2

N-Terminal Sequence Analysis

The hG-CSFs purified by the procedures of Examples <1-> to <1-5> was electrophoresed on a SDS-PAGE gel, and transferred to a PVDF membrane. The transferred membrane was dyed using a Ponceau S solution, and then N-terminal sequence (15 amino acids) was analyzed at the Korea Basic Science Institute (Seoul branch)

As a result, N-terminal sequence of hG-CSF isolated and purified from the recombinant *E. coli* according to the purification method of the present invention was found to be identical to that of native form, and it contains the host-derived proteins of 100 ng/mg or less, the host-derived DNAs of 100 pg/mg or less, and enterotoxin of 10 EU/IU hG-CSF or less.

EXPERIMENTAL EXAMPLE 3

Reversed-Phase High-Pressure Chromatography

The eluate obtained in Example <1-5> was applied to a butylsilyl silica column, and then 0.1% TFA/water and 0.1% TFA/acetonitrile as mobile phase were added to the column to perform reversed-phase high-pressure chromatography. The resulting chromatogram is shown in FIG. 3.

Figure 3:
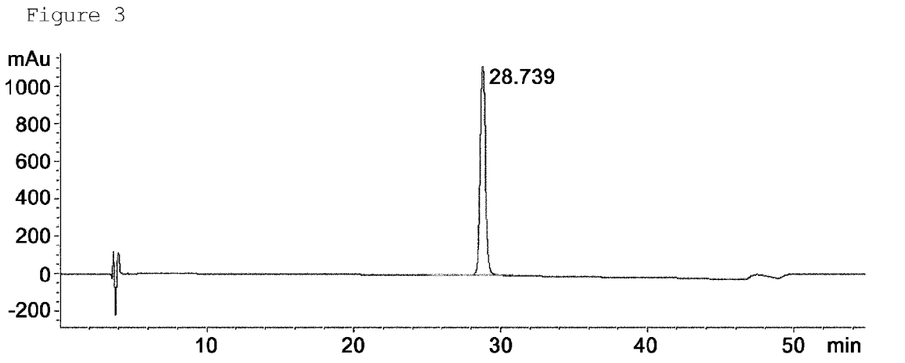
FIG. 3 shows the result of reversed-phase high-pressure chromatography of the column eluate that is obtained by anion exchange chromatography of the purification method of the present invention.

As shown in FIG. 3, the hG-CSFs isolated and purified from the recombinant *E. coli* according to the purification method of the present invention were found to have very high purity by effective removal of microvariants having similar features.

EXPERIMENTAL EXAMPLE 4

Size Exclusion High Pressure Chromatography

The eluate obtained in Example <1-5> was applied to a hydrophilic silica gel column (molecular weight of 20,000 to 200,000), and then 20 mM potassium phosphate (pH 6.0)/200 mM sodium chloride as mobile phase were added to the column to perform size exclusion high pressure chromatography. The resulting chromatogram is shown in FIG. 4.

Figure 4:
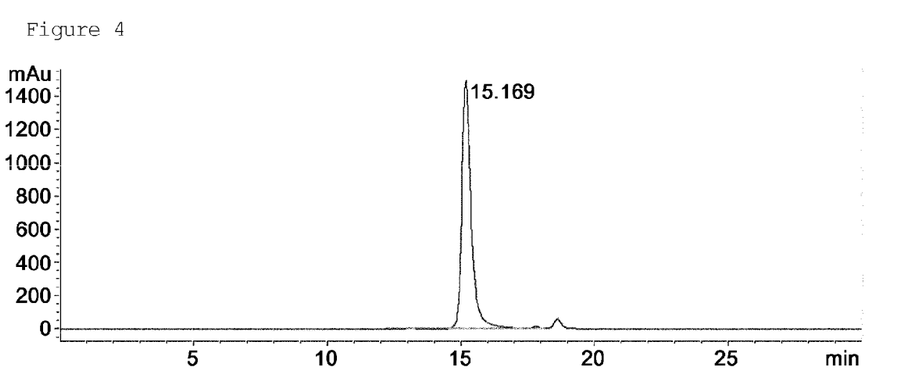
FIG. 4 shows the result of size exclusion high pressure chromatography of the column eluate that is obtained by anion exchange chromatography of the purification method of the present invention.

As shown in FIG. 4, the hG-CSFs isolated and purified from the recombinant *E. coli* according to the purification method of the present invention were found to have very high purity by effective removal of peptides having similar features.

In Experimental Examples 1 to 4, it was confirmed that native hG-CSFs with purity of 99% or higher can be obtained in a yield of 110 mg per 1 L of culture broth of the recombinant *E. coli* according to the purification method of the present invention. As comparison group, hG-CSFs were purified from the recombinant *E. coli* according to the purification method disclosed in Korean Patent No. 356140 (ion exchange resin, adsorption and gel filtration column or antibody column chromatography), and hG-CSFs with purity of 99% or higher were obtained in a yield of 70 mg per 1 L of culture broth. This result indicates that hG-CSFs with purity of 99% or higher can be obtained in a 50% or more improved yield by the purification method of the present invention, compared to the method disclosed in Korean Patent No. 356140.

EXPERIMENTAL EXAMPLE 5

Ex Vivo Potency Test

In order to examine physiological activity of the hG-CSFs obtained according to the purification method of the present invention, hG-CSFs purified in Example <1-5> and an international standard (NIBSC) were subjected to ex vivo potency test in mouse-derived bone marrow cells. Specifically, femurs were dissected from 4 to 6 week-old mice and bone marrow cells were harvested, and then cultured at a proper density. The purified hG-CSFs and international standard sample were mixed with the cultured bone marrow cells by varying the concentration (100.00, 33.33, 11.11, 3.70, 1.23, 0.41, 0.14, 0.05, 0.02, 0.01 ng/ml), and cultured for 2 to 3 days. [Methyl-$H^2$] thymidine was added to the culture media, and the cells were cultured for further 10 to 20 hours. Then, cells were isolated and CPM was measured using a beta-counter. As a result, the hG-CSFs isolated and purified according to the purification method of the present invention were found to satisfy the international standard of 0.6 to $1.4 \times 10^8$ IU/mg.

INDUSTRIAL APPLICABILITY

The method of the present invention can easily purify human granulocyte-colony stimulating factor, identical to the native form expressed in the human body, with high yield and purity without an additional activation process. In particular, according to the method of the present invention, hG-CSF variants expressed in *E. coli* are efficiently removed to obtain physiologically active hG-CSFs with high purity.

The invention claimed is:

1. A method for purifying a human granulocyte-colony stimulating factor (hG-CSF) from a recombinant *Escherichia coli* (*E. coli*) in a high yield, comprising the steps of:
    (a) culturing an hG-CSF-expressing recombinant *E. coli* and subjecting a resulting culture to centrifugation to obtain a first cell pellet;
    (b) separating an hG-CSF-containing supernatant from the first cell pellet obtained in step (a);
    (c) adjusting a pH of the supernatant obtained in step (b) with an acid and separating the resulting precipitate by filtration;
    (d) subjecting a first filtrate obtained in step (c) to cation exchange chromatography to five a first eluate;
    (e) subjecting the first eluate to hydrophobic-interaction chromatography to give a second eluate; and
    (f) subjecting the second eluate to anion exchange chromatography to give a fraction containing hG-CSF.

2. The method according to claim 1, wherein in step (a), the hG-CSF is expressed into the periplasm of recombinant *E. coli*.

3. The method according to claim 2, wherein the recombinant *E. coli* is one or more selected from the group consisting of *E. coli* BL21(DE3)/pT14SS1S17SEG deposited under KCCM-10154, *E. coli* BL21 (DE3)/pTO1S17SG deposited under KCCM-10151, *E. coli* BL21(DE3)/pTO17SG deposited under KCCM-10152, and *E. coli* BL21(DE3)/pBAD2M3VG deposited under KCCM-10153.

4. The method according to claim 1, wherein in step (b), the hG-CSF-containing supernatant is separated from the first cell pellet by osmotic extraction.

5. The method according to claim 4, wherein the osmotic extraction is performed by
treating the first cell pellet with a 10% to 30% sucrose-containing buffer solution and subjecting a resulting mixture to centrifugation to give a second a cell pellet,
adding distilled water to the second cell pellet, and
subjecting a resulting mixture of distilled water and the second cell pellet to centrifugation.

6. The method according to claim 1, wherein in step (c), pH of the supernatant is adjusted to 5.0 to 5.8.

7. The method according to claim 1, wherein the acid of step (c) is selected from the group consisting of acetic acid, phosphoric acid, and citric acid.

8. The method according to claim 1, wherein the cation exchange chromatography of step (d) is performed using a column selected from the group consisting of cross-linked agarose column, cross-linked dextran column, agarose, cellulose column, polystyrene, polyacrylate, cellulose, and silica column.

9. The method according to claim 8, wherein the cation exchange chromatography of step (d) is performed using cross-linked agarose column.

10. The method according to claim 1, wherein the cation exchange chromatography of step (d) is performed using an acetic acid-containing buffer solution within the pH ranging from pH 4.0 to 6.0 having a salt concentration of 200 to 500 mM.

11. The method according to claim 10, wherein the cation exchange chromatography of step (d) is performed using a buffer solution containing 200 to 500 mM sodium chloride and 5 to 20 mM sodium acetate at pH 5.0 to 6.0.

12. The method according to claim 1, wherein the hydrophobic-interaction chromatography of step (e) is performed using an agarose column which has a functional group selected from the group consisting of propyl, butyl, pentyl, hexyl, heptyl and octyl, isoalkyl, neoalkyl, and oligoethylene glycol.

13. The method according to claim 12, wherein the agarose column has a butyl functional group.

14. The method according to claim 1, wherein the hydrophobic-interaction chromatography of step (e) is performed using a buffer solution within the pH ranging from pH 7.0 to 8.5 having a salt concentration of 0 to 100 mM.

15. The method according to claim 14, wherein the hydrophobic-interaction chromatography of step (e) is performed using a buffer solution containing 5 to 20 mM Tris at pH 7.0 to 8.0.

16. The method according to claim 1, wherein the anion exchange chromatography of step (f) is performed using a column selected from the group consisting of a cross-linked agarose column, polymethacrylate resin column, hydrogel column, and cross-linked polymethacrylate resin column.

17. The method according to claim 16, wherein the anion exchange chromatography of step (f) is performed using a cross-linked agarose column.

18. The method according to claim 1, wherein the anion exchange chromatography of step (f) is performed using a buffer solution within the pH ranging from pH 6.5 to 8.5 having a salt concentration of 100 to 300 mM.

19. The method according to claim 18, wherein the anion exchange chromatography of step (f) is performed using a buffer solution containing 100 to 300 mM sodium chloride, 5 to 20 mM Tris, and 50 to 200 mM urea at pH 7.0 to 8.0.

\* \* \* \* \*